United States Patent
Roop et al.

(10) Patent No.: US 9,927,392 B2
(45) Date of Patent: Mar. 27, 2018

(54) SENSING FIELD EFFECT TRANSISTOR DEVICES, SYSTEMS IN WHICH THEY ARE INCORPORATED, AND METHODS OF THEIR FABRICATION

(71) Applicants: Raymond M. Roop, Paradise Valley, AZ (US); Jose Fernandez Villasenor, Tokyo (JP); Stephen R. Hooper, Mesa, AZ (US); Patrice M. Parris, Phoenix, AZ (US)

(72) Inventors: Raymond M. Roop, Paradise Valley, AZ (US); Jose Fernandez Villasenor, Tokyo (JP); Stephen R. Hooper, Mesa, AZ (US); Patrice M. Parris, Phoenix, AZ (US)

(73) Assignee: NXP USA, INC., Austin, TX (US)

( * ) Notice: Subject to any disclaimer, the term of this patent is extended or adjusted under 35 U.S.C. 154(b) by 274 days.

(21) Appl. No.: 14/459,841

(22) Filed: Aug. 14, 2014

(65) Prior Publication Data

US 2016/0047775 A1 Feb. 18, 2016

(51) Int. Cl.
*G01N 27/414* (2006.01)
*H05K 3/10* (2006.01)

(52) U.S. Cl.
CPC .................. *G01N 27/4148* (2013.01)

(58) Field of Classification Search
CPC .............. G01N 27/4148; H05K 3/10
See application file for complete search history.

(56) References Cited

U.S. PATENT DOCUMENTS

| 4,020,830 | A | * | 5/1977 | Johnson | ............. | A61B 5/14532 |
| | | | | | | 204/403.1 |
| 4,505,799 | A | | 3/1985 | Baxter | | |
| 5,833,824 | A | | 11/1998 | Benton | | |
| 2007/0096165 | A1 | * | 5/2007 | Lipisko | ............. | G01N 27/4148 |
| | | | | | | 257/253 |

OTHER PUBLICATIONS

Parizi, K., et al, "Exceeding Nernst Limit (59m/V/pH): CMOS-Based pH Sensor for Autonomous Applications", 2012 IEEE International Electron Devices Meeting, Dec. 2012, pp. 24.7.1-24.7.4.
(Continued)

*Primary Examiner* — Robert Carpenter
(74) *Attorney, Agent, or Firm* — Sherry W. Schumm

(57) ABSTRACT

Embodiments of sensing devices include one or more integrated circuit (IC) die, a housing, and a fluid barrier material. Each IC die includes an electrode-bearing surface and a contact surface. One of the die includes an SFET with a sensing electrode proximate to the electrode-bearing surface. The same or a different die includes a reference electrode proximate to the electrode-bearing surface. The die(s) also include IC contacts at the contact surface(s), and conductive structures coupled between the SFET, the reference electrode, and the IC contacts. The housing includes a mounting surface, and housing contacts formed at the mounting surface. The IC contacts are coupled to the housing contacts. The fluid barrier material is positioned between the mounting surface and the IC die. The fluid barrier material provides a fluid barrier between the IC and housing contacts and a space that encompasses the sensing electrode and the reference electrode.

14 Claims, 4 Drawing Sheets

(56) References Cited

OTHER PUBLICATIONS

Ho, N.J., et al., "Encapsulation of Polymeric Membrane-Based Ion-Selective Field Effect Transistors," Sensors and Actuators, pp. 413-421, 1983.
Sudakov-Boreysha, L, et al., "ISFET CMOS Compatible Design and Encapsulation Challenges," Proceedings of the 2004 11th IEEE International Conference on Electronics, Circuits and Systems, pp. 535-538, Dec. 2004.
Jimenez-Jorquera, C., et al., "ISFET Based Microsensors for Environmental Monitoring," Sensors 10, No. 1, pp. 61-83, Dec. 2009.
Bergveld, IR. P., "Isfet, Theory and Practice," IEEE Sensor Conference, Toronto, pp. 1-26, Oct. 2003.
Cane, C., et al., "Microtechnologies for pH ISFET Chemical Sensors," Microelectronics Journal, pp. 389-405, May 1997.
Hamamatsu Photonics K.K., Electro Tube Division,"Stealth Dicing Technology and Applications, Technical Information; TLAS9004E01", pp. 1-8 (Mar. 2005).

\* cited by examiner

SENSING FIELD EFFECT TRANSISTOR DEVICES, SYSTEMS IN WHICH THEY ARE INCORPORATED, AND METHODS OF THEIR FABRICATION

TECHNICAL FIELD

Embodiments of the subject matter described herein relate generally to semiconductor devices, and more particularly relate to sensing field effect transistors (SFETs) and systems in which they are incorporated.

BACKGROUND

Field effect transistors (FETs) can be used in sensors configured to detect and analyze chemical substances and biological agents within fluids. Typically, these sensors rely on the voltage developed between the gate and a reference electrode. More particularly, changes in the gate bias result in a change in the channel current flowing through the device. In some designs, a fluid being sensed is in intimate contact with the gate dielectric. In other designs, the fluid being sensed is separated from the gate dielectric by a sensitive membrane or coating (e.g., a layer or coating applied to the gate dielectric). For example, depending on the application and the type of sensitive membrane or coating overlying the gate dielectric, these devices may be termed ion-sensitive field effect transistors (ISFETS), immunological field effect transistors (IMFETS) or enzyme field effect transistors (ENFETS).

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Embodiments of the inventive subject matter include sensing devices (referred to below as SFET devices), methods of their manufacture, and systems within which such sensing devices are incorporated. The sensing device embodiments described herein each include at least one field effect transistor (FET) and a reference electrode. In some embodiments, the sensing device also may include a reference FET (REFET), which enables the sensing device to perform differential sensing. The sensing electrodes of one or both FETs may be coated or covered with a sensitive material on which a charge can be induced that varies when the sensitive material is exposed to a chemical substance or biological agent to which it is sensitive. The change in the charge of the sensitive material, in turn, affects the charge on the sensing electrode and the gate. For example, various embodiments include sensing devices that include one or more ion-sensitive field effect transistors (ISFETS), immunological field effect transistors (IMFETS), enzyme field effect transistors (ENFETS), or other types of FETs that are affected by chemical substances and/or biological agents in a fluid that contacts the sensing electrodes or sensitive materials of the FETs. These devices may be generically referred to herein as sensing FETs (SFETs). As will be made clearer from the following description, chip-scale implementation of the components of an SFET device, along with specialized packaging and the use of appropriate fluid barrier materials enables highly-reliable SFET devices to be easily and inexpensively mass produced.

A device that includes an SFET (e.g., a single FET or an FET/REFET combination) and its associated reference electrode may be incorporated into a system that is configured to detect and process the electrical signals produced by the SFET(s) and the reference electrode. Accordingly, such systems may produce measurement data indicating the presence of or representing the concentration of a chemical substance or biological agent in a fluid that is applied to the device.

Figure 1:
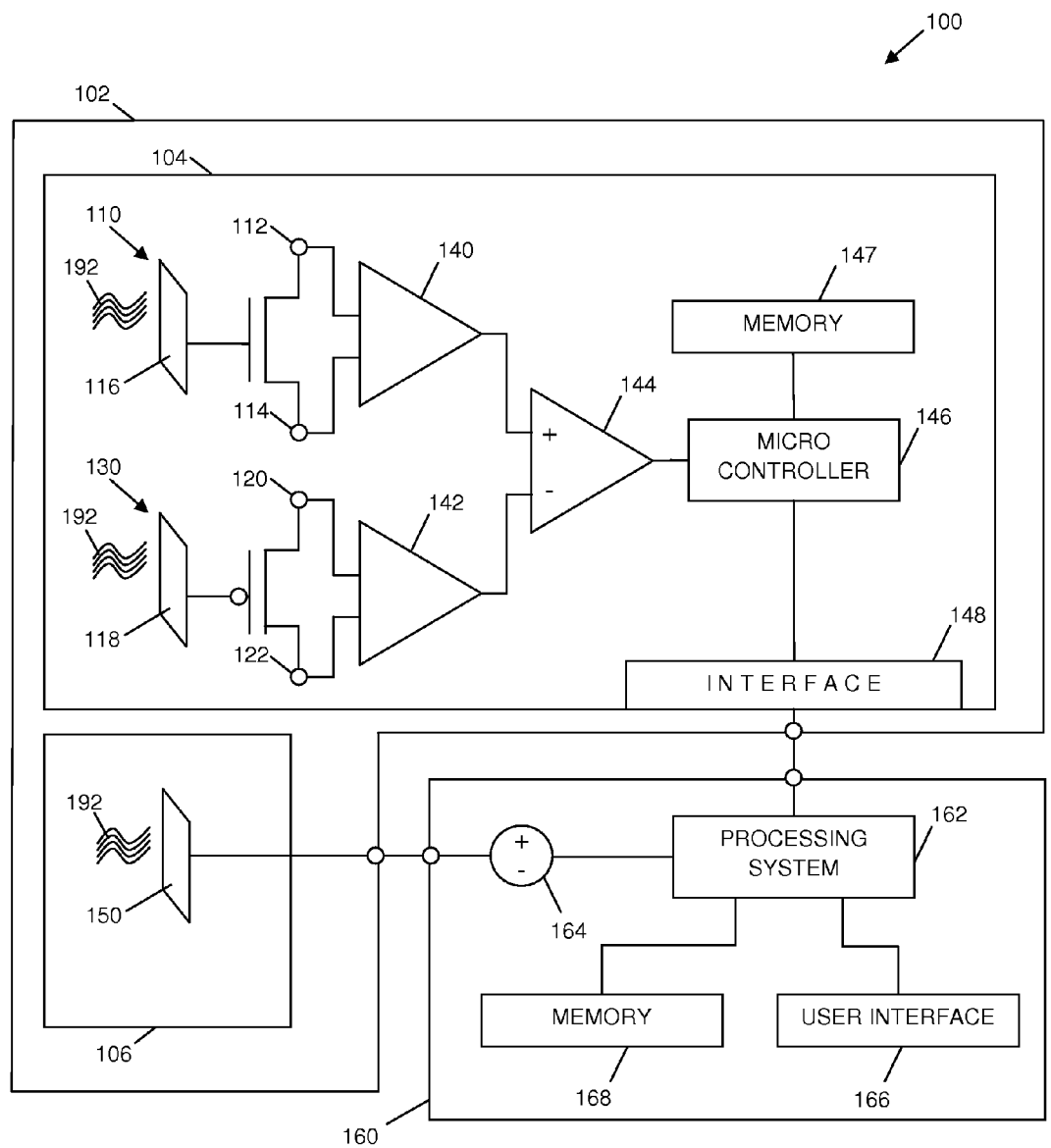
FIG. 1 is schematic diagram of a sensing field effect transistor (SFET) device coupled with a measurement system, in accordance with an example embodiment.

For example, FIG. 1 is schematic diagram of a system 100 that includes an SFET device 102 coupled with a measurement system 160, in accordance with an example embodiment. SFET device 102 includes two SFETs 110, 130 that provide differential signals that are further analyzed by other components of the system 100. More specifically, in an embodiment, SFET device 102 has a FET/REFET configuration, in that the SFET device 102 includes a first SFET 110 and a reference SFET 130 (REFET). According to an embodiment, the REFET and its corresponding REFET electrode 118 may be configured to be less sensitive to the chemical substances and/or biological agents than are the first SFET 110 and its corresponding sensing electrode 116.

The first SFET 110 has a gate, source, and drain, where the gate is electrically coupled to a sensing electrode 116 (e.g., either directly or through a gate contact), and the source and drain are coupled to source and drain contacts 112, 114, respectively. The sensing electrode 116 may directly contact a fluid 192 being tested, or a sensitive material (not shown in FIG. 1) may overlay the sensing electrode 116. Either way, exposure to the fluid 192 may induce charge in the sensitive material and the sensing electrode, which in turn affects the charge on the gate of SFET 110 and the current flowing through a channel underlying the gate.

Similarly, the REFET (or SFET 130) has a gate, source, and drain, where the gate is electrically coupled to a REFET electrode 118 (e.g., either directly or through a gate contact), and the source and drain are coupled to source and drain contacts 120, 122, respectively. Again, the REFET electrode 118 may directly contact the fluid 192 being tested, or a sensitive material (not shown in FIG. 1) may overlay the REFET electrode 118. Either way, exposure to the fluid 192 may induce charge in the sensitive material and the sensing electrode, which in turn affects the charge on the gate of SFET 130 and the current flowing through a channel underlying the gate. In yet another embodiment, the REFET electrode 118 or the sensitive material covering it (not shown in FIG. 1) may be exposed to a different fluid (e.g., a reference fluid) while sensing electrode 116 or the sensitive material covering it (also not shown in FIG. 1) is being exposed to fluid 192.

According to an embodiment, SFETs 110, 130 may have opposite conductivity types, as illustrated in FIG. 1. For example, SFET 110 may be an n-channel (or n-type) FET, and SFET 130 may be a p-channel (or p-type) FET, or vice versa. In an alternate embodiment, SFETs 110, 130 may have the same conductivity type (e.g., either both n-type or both p-type). In such an embodiment, the characteristics of the SFETs 110, 130 and or the sensing and REFET electrodes 116, 118 to which they are coupled may differ to enhance the ability of the SFETs 110, 130 to produce signals having measurable differences. In still other alternate embodiments, SFET device 102 may include only a single SFET, or may include more than two SFETs.

In addition, the sensing and REFET electrode 116, 118 and SFET 110, 130 configurations illustrated in FIG. 1 represent simplified electrical representations of sensing electrode/SFET combinations. In other embodiments, either or both of the electrodes 116, 118 may be capacitively coupled to the SFETs 110, 130 (e.g., the gates of the SFETs 110, 130 may be floating), and/or the SFETs 110, 130 may include additional structures that affect operation of the SFETs 110, 130 (e.g., control structures that may be used to affect the biasing of the gate, protection diodes, and so on). Various configurations of sensing electrodes and SFETs are intended to be included within the scope of the inventive subject matter.

In the illustrated embodiment of the FET/REFET configuration, and according to an embodiment, the source and drain contacts 112, 114, 120, 122 of SFETs 110, 130 are coupled to voltage or current measurement devices 140, 142. Each measurement device 140, 142 includes two inputs coupled across the source and drain contacts 112, 114, 120, 122 of one of the SFETs 110, 130, and each measurement device 140, 142 is configured to measure either the drain-source voltage (Vds) or the drain-source current (Ids) of the SFET 110, 130 to which it is coupled. Further, each measurement device 140, 142 produces a voltage signal at an output of the device 140, 142, where the voltage signal is representative of the measured Vds or Ids.

According to an embodiment, the outputs of the measurement devices 140, 142 are coupled to a non-inverting input and an inverting input of an operational amplifier 144, which is configured to detect and amplify the difference between the two voltage signals. According to an embodiment, an analog signal is produced at the output of operational amplifier 144, which represents the difference between the two voltage signals.

Device 102 further includes a microcontroller 146, in an embodiment, which receives the analog signal produced by the operational amplifier 144, and which converts the analog signal into a digital signal that indicates the difference between the two voltage signals produced by the SFETS 110, 130 and measurement devices 140, 142. This digital signal may be output from the device 102 through a digital interface 148, such as a serial-peripheral interface (SPI), and I2C interface, or the like. The digital interface 148, in turn, is coupled (e.g., through contacts 228, 428, FIGS. 2, 4) to measurement system 160, the components of and functionality of which will be described below. In an alternate embodiment, the analog signal produced by the operational amplifier 144 may be output from the device 102 directly.

Device 102 also may include memory 147, which may be configured to store digital representations of the output of the operational amplifier 144, the voltage signals produced by the SFETs 110, 130, and/or other information. For example, SFET device 102 may be capable of performing its essential measurement operations prior to being connected to measurement system 160. After subsequent coupling of the SFET device 102 to measurement system 160, the information stored within memory 147 may be downloaded to measurement system 160.

According to an embodiment, device 102 also includes a reference electrode 150, which may be used to provide an electrical bias to the fluid 192 being tested. According to an embodiment, reference electrode 150 also is coupled to measurement system 160, and reference electrode 150 may receive a bias voltage directly from measurement system 160. In an alternate embodiment, reference electrode 150 may receive a bias voltage from microcontroller 146, or from another component of SFET device 102.

As will be explained in more detail later, the components of SFET device 102 may be packaged together in a common housing, and may be implemented on one or more integrated circuit (IC) die. For example, as illustrated in FIG. 1, electrodes 116, 118, SFETS 110, 130, measurement devices 140, 142, operational amplifier 144, microcontroller 146, and interface 148 all may be implemented on a first IC die 104, and reference electrode 150 may be implemented on a second IC die 106. In an alternate embodiment, all of the components of SFET device 102 may be implemented on a single IC die (e.g., as in the embodiment of FIG. 4). In still other alternate embodiments, SFETs 110, 130 may be implemented on separate IC die, and/or either SFET 110, 130 may be implemented on the same die as reference electrode 150. In still other alternate embodiments, any of measurement devices 140, 142, operational amplifier 144, microcontroller 146, and/or interface 148 may be implemented on separate IC die from SFETs 110, 130.

Although not illustrated, SFET device 102 may include additional components, including for example, contacts for receiving power and ground from an external system (e.g., from measurement system 160), a limited or rechargeable power source (e.g., a battery system), and so on. Alternatively, SFET device 102 may include fewer than all of the illustrated components. For example, some or all of measurement devices 140, 142, operational amplifier 144, and/or microcontroller 146 may be excluded from SFET device 102, and may instead be implemented within measurement system 160.

According to an embodiment, measurement system 160 includes a processing system 162, a user interface 166 (e.g., including a display, keypad, and so on), memory 168, and a bias voltage generator 164. Among other things, processing system 162 is configured to cause bias voltage generator 164 to provide a bias voltage to reference electrode 150. According to various embodiments, the bias voltage may be a direct current (DC) voltage or an alternating current (AC) voltage. The characteristics of the bias voltage may be specified by a user through user interface 166, and/or may be stored in memory 168, for example.

Further, processing system 162 is configured to receive signals from SFET device 102 (e.g., through interface 148). As discussed previously, the signals represent the measured differential voltage produced by operational amplifier 144. Processing system 162 is further configured to store the measured differential voltages in memory 168 and/or to output indications of the measured differential voltages using user interface 166.

According to an embodiment, SFET device 102 may be coupled to and uncoupled from measurement system 160 by a user. For example, SFET device 102 may be packaged in a housing that is configured to snap into a correspondingly shaped receptacle within measurement system 160. Alternatively, SFET device 102 may be permanently coupled to measurement system 160 with hardwired or persistent connections. In still another embodiment, SFET device 102 and measurement system 160 may communicate over a Near Field Communication (NFC), radio frequency (RF) or wireless communication link. In such an embodiment, SFET device 102 could include the capability to function autonomously (e.g., SFET device 102 would be configured to provide a bias voltage to reference electrode 150 and to perform the other sensing and processing steps previously described).

As described previously, the essential purpose of SFET device 102 is to detect chemical substances and/or biological agents in a fluid 192 that is brought into contact with sensing electrode 116, reference electrode 150, and, in some embodiments, REFET electrode 118. Of course, the various electrical contacts of the IC die and the interfaces with the measurement system 160 should be protected from the fluid 192 being tested, in order to avoid short circuits that would compromise the functionality of the system 100. According to various embodiments, the IC die 104, 106 of SFET device 102 are implemented with bottom-surface contacts (e.g., contacts 228, 246, 428, FIGS. 2, 4) that are protected during operation by a fluid barrier material (e.g., fluid barrier material 280, 380, 480, FIGS. 2-4).

Figure 2:
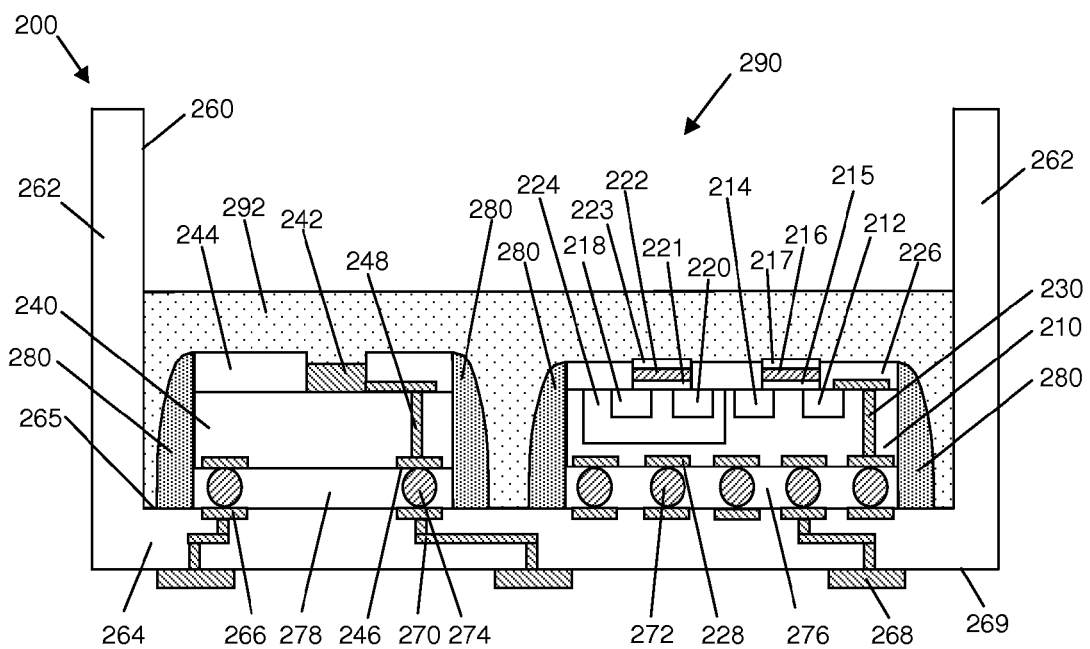
FIG. 2 is a cross-sectional, side view of an SFET device, in accordance with an example embodiment.

FIG. 2 is a cross-sectional, side view of an SFET device 200 (e.g., SFET device 102, FIG. 1), in accordance with an example embodiment. SFET device 200 includes SFET IC 210, reference electrode IC 240, and package housing 260. SFET IC 210 and reference electrode IC 240 are electrically and mechanically coupled to package housing 260, and, more specifically, to a mounting surface 265 of a bottom member 264 of package housing 260. As will be described in more detail below, SFET device 200 further includes fluid barrier material 280 disposed between the mounting surface 265 and sidewalls of SFET IC 210 and reference electrode IC 240, where the fluid barrier material 280 is configured to protect contacts 228, 246, 266 on surfaces of the SFET IC 210, reference electrode IC 240, and mounting surface 265 from fluid 292 that is being tested by the SFET device 200.

The SFET IC 210 illustrated in FIG. 2 is a simplified depiction of an IC that includes a first SFET and a second SFET, referred to below as a first SFET and a REFET, respectively. For example, the first SFET and the REFET may correspond, schematically, to SFETS 110, 130 of FIG. 1, respectively. As will be explained in more detail later, SFET IC 210 may have a different and/or more complicated configuration than that depicted in FIG. 2.

The first SFET and the REFET are formed in and over a semiconductor substrate, which may be a silicon substrate, a silicon-on-insulator (SOI) substrate, a gallium nitride substrate, a gallium arsenide substrate, a substrate of a different semiconductor material, or a compound substrate (e.g., silicon on sapphire, and so on). According to an embodiment, the SFET IC 210 is a complementary metal oxide semiconductor (CMOS) IC, which includes active devices of both p-type and n-type conductivity. For example, the first SFET may be a p-channel device, and the REFET may be an n-channel device, or vice versa. Alternatively, the first SFET and the REFET may have the same conductivity or channel type. In the description below, the first SFET is described as being formed directly in the semiconductor substrate. In contrast, the REFET is described as being formed in a well 224 that extends into the semiconductor substrate, where the well 224 has an opposite conductivity type from the semiconductor substrate. In alternate embodiments, both the first SFET and the REFET (including the well 224) may be formed in a "tub" within the substrate, where the "tub" is a region of different doping type or concentration from the semiconductor substrate. These and other modifications are intended to fall within the scope of the inventive subject matter.

According to an embodiment, the portion of the semiconductor substrate within which the first SFET is formed has a first conductivity type and doping density. For example, this portion of the semiconductor substrate may have a p-conductivity type and relative doping density. Conversely, the portion of the semiconductor substrate within which the REFET is formed has a second conductivity type. Accordingly, SFET IC 210 further may include a well 224 that is doped to have a second conductivity type that is opposite the first conductivity type. For example, according to an embodiment, the well 224 may have an n conductivity type and relative doping density.

According to an embodiment, the first SFET includes a first source region 212 and a first drain region 214, each of the second conductivity type, which are formed at the surface of the semiconductor substrate. A channel is present between the source and drain regions 212, 214, and a gate dielectric 215 overlies the channel. A gate contact (e.g., sensing electrode 216 or a gate contact electrically coupled to sensing electrode 216) may overlay the gate dielectric 215. In some cases, the gate dielectric 215 or another dielectric may be in direct contact with the fluid 292. According to the embodiment illustrated in FIG. 2, the gate contact also functions as a sensing electrode 216. In an alternate embodiment, the gate contact and the sensing electrode 216 may be distinct features of the first SFET, and may be electrically coupled together (e.g., through one or more vias, conductive layers, capacitors, and so on). Either way, the sensing electrode 216 is formed proximate to an "electrode-bearing" surface of the SFET IC 210 (i.e., the top surface, in the orientation of FIG. 2). As used herein, "proximate to" a surface means co-planar with the surface, slightly above the surface, or slightly below the surface. The top surface of the substrate and structures proximate to the electrode-bearing surface may be electrically isolated from each other and/or protected by a protection or passivation layer 226.

Similarly, the REFET includes a second source region 218 and a second drain region 220, each of the first conductivity type, which are formed at the surface of the semiconductor substrate in the second conductivity type well 224. A channel is present between the source and drain regions 218, 220, and a gate dielectric 221 overlies the channel. A gate contact (e.g., REFET electrode 222 or a gate contact electrically coupled to REFET electrode 222) overlies the gate dielectric 221. In an alternate embodiment, the gate contact and the REFET electrode 222 may be distinct features of the first SFET, and may be electrically coupled together (e.g., through one or more vias, conductive layers, capacitors, and so on). Either way, the REFET electrode 222 also is formed proximate to the electrode-bearing surface of the SFET IC 210.

According to an embodiment, sensitive material 217, 223 overlies both of the electrodes 216, 222. As discussed previously, a charge is induced on the sensitive material 217, 223 that varies when the sensitive material 217, 223 is exposed to a chemical substance or biological agent (within fluid 292) to which it is sensitive. In various embodiments, the sensitive material 217, 223 may be selected from a biological material sensitive material, a pH sensitive material, a chemical sensitive material, and an ion sensitive material. More specifically, the sensitive material 217, 223 may include one or more materials that are selected from silicon nitride, polyvinyl chloride (PVC) compounds (e.g., PVC-based membranes), an enzyme, an antibody, an antigen, ribonucleic acid (RNA), deoxyribonucleic acid (DNA), DNA-like fragments, epitopes, and cell receptors. Other suitable sensitive materials may be used in other embodiments.

The charges induced in the sensitive material 217, 223, in turn, affect the charges on the electrodes 216, 222 and the gate contacts. The charges on the electrodes 216, 222 and the gate contacts affect the drain-source voltage, Vds, and/or the amount of current through the channels of the first FET and the REFET (i.e., the drain-source current, Ids, or more specifically the amount of current flowing between source 212 and drain 214, and the amount of current flowing between source 218 and drain 220). For example, if Vds is constant, the change in the gate chare causes Ids to change. Conversely, if Ids is constant, the change in the gate charge causes Vds to change. The variable drain-source currents and/or drain source voltages may be measured and processed (e.g., by measurement devices 140, 142, operational amplifier 144, microcontroller 146, and so on) to produce indications of the presence of or concentrations of chemical substances and/or biological materials present in the fluid 292.

In embodiments in which the sensitive material 217, 223 covers both the sensing electrode 216 and the REFET electrode 222, one of the electrodes 216, 222 may be larger than the other to facilitate differential sensing. This is done by extending the gate of one of the devices while maintaining the structure of the underlying FET. This increases the charge collected and, hence, the gate bias. In an alternate embodiment, differential sensing may be facilitated by excluding the sensitive material 217, 223 from either or both of the electrodes 216, 222, or by including an insensitive material on the REFET electrode 222. In another alternate embodiment, the gate of one of the devices may be extended while maintaining the structure of the underlying FET.

Although some important features of the first SFET and the REFET are depicted in FIG. 2, it is to be understood that the first SFET and the REFET may have more complicated and/or different configurations in an actual implementation. For example, although the first SFET and the REFET each are depicted as including an electrode 216, 222 directly overlying gate dielectric 215, 221, in alternate embodiments, the electrodes 216, 222 may be formed in an upper metal layer, while a separate gate contact may be formed in a lower metal layer (i.e., in a metal layer overlying the gate dielectric 215, 221), and the distinct sense and gate contact metal layers may be interconnected with conductive vias and through one or more intervening metal layers. Further, as indicated above in conjunction with the description of FIG. 1, the electrodes 216, 222 may be capacitively coupled to their respective gate contacts. These and other modifications are intended to fall within the scope of the inventive subject matter.

Further, as also discussed in conjunction with the description of FIG. 1, the SFET IC 210 also may include one or more measurement devices (e.g., devices 140, 142), operational amplifiers (e.g., operational amplifier 144), microcontrollers (e.g., microcontroller 146), interfaces (e.g., interface 148), or other components. Alternatively, some or all of these components may be provided in other ICs that form a portion of the SFET device 200, or some or all of these components may be implemented external to the SFET device 200 (e.g., in a measurement system 160).

Either way, the first SFET and the REFET (or more specifically their sources and drains) are coupled to a plurality of contacts 228 at a contact surface of the SFET IC 210, in an embodiment, where the contact surface is on an opposite side of the SFET IC 210 from the electrode-bearing surface. Electrical coupling between the first SFET and the REFET to the plurality of contacts 228 may be direct, or may be made through one or more other components formed in the SFET IC 210 (e.g., through measurement devices 140, 142, operational amplifier 144, microcontroller 146, interface 148, and/or other components). The electrical connections to the first SFET and the REFET may include, for example, conductive routing within one or more metal layers and, in a particular embodiment, one or more through substrate vias 230 (TSVs), which extend through the substrate to electrically couple components proximate to the electrode-bearing surface and the contacts 228 proximate to the contact surface. In an alternate embodiment, the FET and REFET may be formed proximate to the contact surface (i.e., the bottom surface of SFET IC 210, in the orientation of FIG. 2. In other words, the substrate may be flipped, with respect to the orientation shown in FIG. 2), and TSVs or other electrical structures may be used to electrically couple the gate contacts of the FET and REFET to a sensing electrode and a REFET electrode at the electrode-bearing surface (i.e., the top surface of the SFET IC 210, in the orientation of FIG. 2).

Referring now to reference electrode IC 240, reference electrode IC 240 includes a reference electrode (e.g., reference electrode 150, FIG. 1) formed on or above a semiconductor substrate. The top surface of the substrate and structures proximate to the electrode-bearing surface may be electrically isolated from each other and/or protected by a protection or passivation layer 244. The reference electrode IC also includes one or more contacts 246 at a contact surface of the reference electrode IC 240, where the contact surface is on an opposite side of the reference electrode IC 240 from the electrode-bearing surface. The reference electrode 242 is electrically coupled to at least one of the one or more contacts 246 through conductive routing within one or more metal layers and, in a particular embodiment, one or more TSVs 248, which extend through the substrate to electrically couple components proximate to the electrode-bearing surface and the contacts 246 proximate to the contact surface.

Referring now to package housing 260, and as mentioned previously, housing 260 includes a bottom member 264 with a mounting surface 265. In addition, housing 260 includes a plurality of first contacts 266 formed at the mounting surface 265, a plurality of second contacts 268 formed at an exterior surface 269 of the package housing 260, one or more conductive routing layers 270 between the mounting and exterior surfaces 265, 269, and conductive vias (not numbered) interconnecting the contacts 266, 268 and conductive layers 270.

According to an embodiment, package housing 260 also may include sidewalls 262 extending from the mounting surface 265. The sidewalls 262 and mounting surface 265 define a cavity 290 within which the SFET IC 210, the reference electrode IC 240, and a liquid 292 being tested are contained. According to an embodiment, the height of the sidewalls 262 extends above the electrode-bearing surfaces of the SFET IC 210 and the reference electrode IC 240. In alternate embodiments, the height 262 of the sidewalls 262 may be at or below the heights of the electrode-bearing surfaces of the SFET IC 210 and the reference electrode IC 240. In still another alternate embodiment, the sidewalls 262 may be excluded (e.g., surface tension of the liquid 292 may enable the liquid 292 to cover the sensing and REFET electrodes 216, 222 and the reference electrode 242).

Contacts 228, 246 of the SFET IC 210 and the reference electrode IC 240 are electrically and physically coupled to sets of corresponding contacts 266 on the mounting surface 265. For example, the IC contacts 228, 246 may be coupled to the housing contacts 266 with solder balls 272, 274, conductive epoxy, or by other means. In the case of solder ball connections, either or both sets of solder balls 272, 274 may be reflowed to establish the electrical and physical connection. Alternatively, either or both sets of solder balls 272, 274 may be press-fit to corresponding pins (not shown) associated with contacts 266 or 228, 246 to provide the electrical connection, and the SFET IC 210 and/or reference electrode IC 240 may be clamped to housing 260 to establish a robust physical connection.

In any event, according to an embodiment, SFET device 200 also includes a fluid barrier material 280 between the mounting surface 265 and the SFET and reference electrode ICs 210, 240, where the fluid barrier material 280 is configured to provide a fluid barrier between contacts 228, 246, 266 and a space (e.g., within cavity 290 or otherwise overlying the SFET and reference electrode ICs 210, 240) that encompasses the sensing and REFET electrodes 216, 222 and the reference electrode 242. For example, in the illustrated embodiment, the fluid barrier material 280 is selectively deposited between sidewalls of the SFET and reference electrode ICs 210, 240 and the mounting surface 265, where portions of the mounting surface 265 may remain uncovered. According to an embodiment, the fluid barrier material 280 may be configured to maintain cavities 276, 278 between the SFET and reference electrode ICs 210, 240 and the mounting surface 265, or the fluid barrier material 280 may fill these cavities 276, 278, as long as the fluid barrier material 280 is sufficiently electrically insulating. For example, fluid barrier material 280 may include silicone (e.g., a room temperature vulcanizing silicone), fluorosilicone, perfluoropolyether, epoxy, polyurethane, underfill material, or another material that is suitable for providing a fluid barrier between the contacts 228, 246, 266 and the fluid 292.

In the above-described embodiment, both the SFET electrodes 216, 222 and the reference electrode 242 may be exposed to fluid 292 in the space that encompasses the electrodes 216, 222, 242. In an alternate embodiment, the REFET electrode 222 and/or the reference electrode 242 instead may be formed proximate the contact surface of the SFET IC 210 and/or the reference electrode IC 240, respectively, so that the REFET electrode 222 and/or the reference electrode 242 is exposed to the cavity 276 or 278 underlying the contact surface. In such an embodiment, cavity 276 and/or 278 may be filled with a non-conductive reference fluid (not illustrated) that has known electrical characteristics. In the embodiment in which the REFET electrode 222 is so arranged, the REFET electrode 222 may be electrically coupled with the REFET through one or more TSVs.

Figure 3:
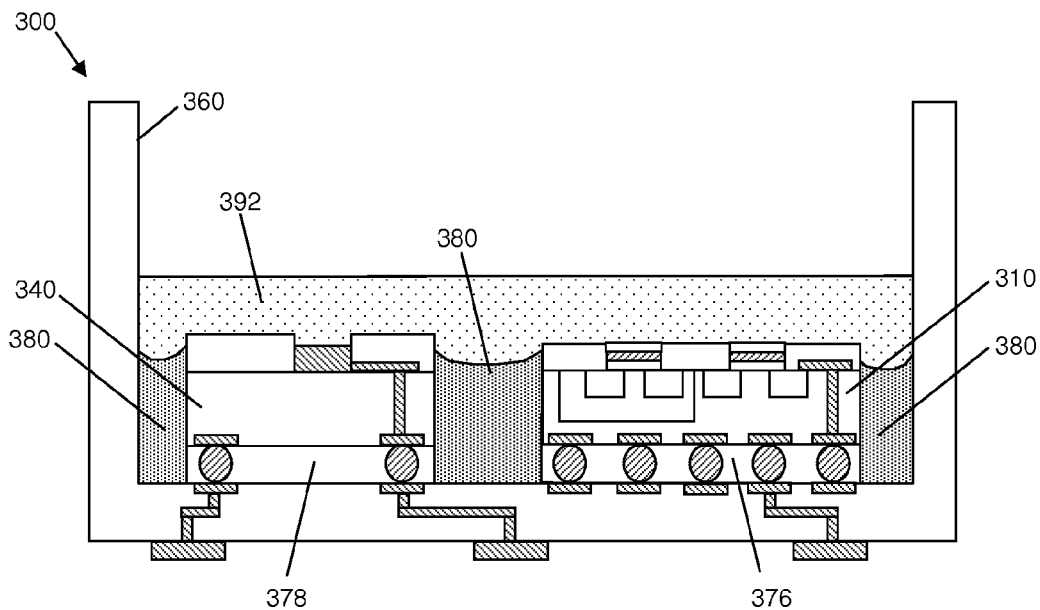
FIG. 3 is a cross-sectional, side view of an SFET device, in accordance with another example embodiment.

In the embodiment of FIG. 2, the fluid barrier material 280 is configured so that portions of the mounting surface 265 remain exposed to fluid 292 deposited within cavity 290. FIG. 3 is a cross-sectional, side view of an SFET device 300, in accordance with another example embodiment. Similar to the previously described SFET device 200, the SFET device 300 illustrated in FIG. 3 includes a package housing 360, and an SFET IC 310 and reference electrode IC 340 coupled to a mounting surface of the package housing 360. However, in the embodiment of FIG. 3, the fluid barrier material 380 deposited within the package housing 360 covers an entirety of the mounting surface of the package housing 360, and extends up the sidewalls of the SFET and reference electrode ICs 310, 340. For example, fluid barrier material 380 may include one of the aforementioned materials, or may include a gel or other suitably viscous and compliant material. Again, the fluid barrier material 380 may be configured to maintain cavities 376, 378 between the SFET and reference electrode ICs 310, 340 and the mounting surface, or the fluid barrier material 380 may fill these cavities 376, 378, as long as the fluid barrier material 380 is sufficiently electrically insulating.

In the embodiments of FIGS. 2 and 3, the first FET and REFET are formed in one IC die 210, 310, and the reference electrode is formed in another, distinct IC die 240, 340. An advantage that this configuration provides is that the IC die 240, 340 that includes the reference electrode may be fabricated without accounting for the sensitive material (e.g., sensitive material 217, 223) overlying the first FET and REFET electrodes, and the IC die 210, 310 that includes the first FET and the REFET may be fabricated without considering how the reference electrode will be fabricated without overlying sensitive material. Further, the IC die 240, 340 that includes the reference electrode may be electrically and mechanically coupled to the housing 260 using a relatively high temperature process, rather than being constrained to using a process having a lower temperature that would not potentially damage the sensitive material overlying the FET and REFET electrodes.

Figure 4:
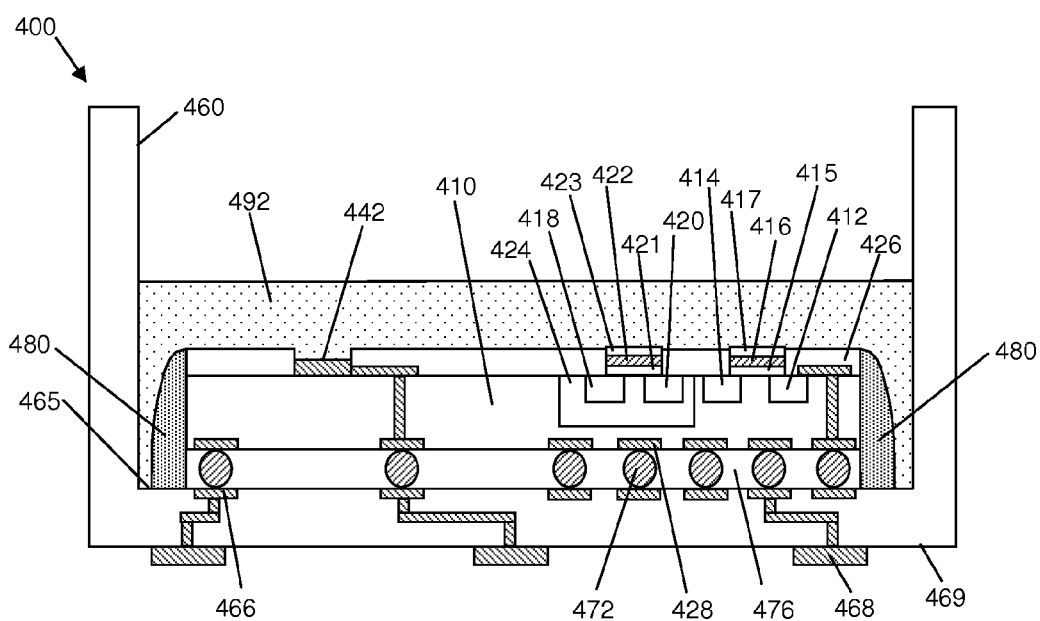
FIG. 4 is a cross-sectional, side view of an SFET device, in accordance with yet another example embodiment.

In an alternate embodiment, however, the first FET, the REFET, and the reference electrode all may be formed in a single die. Such an embodiment may be relatively easy to fabricate, for example, when the sensitive material overlying the FET and REFET electrodes may be easily patterned and removed (e.g., as is the case for Si3N4 and other materials), and/or when masking operations may easily be performed to mask the reference electrode while the sensitive material is deposited on the FET and REFET electrodes. For example, FIG. 4 is a cross-sectional, side view of an SFET device 400, in accordance with yet another example embodiment. SFET device 400 includes SFET and reference electrode die 410 coupled to a package housing 460. As many of the previously described details and alternate embodiments described in conjunction with FIGS. 2 and 3 apply equally to FIG. 4, such details and alternate embodiments are not repeated in conjunction with the description of FIG. 4 for the purpose of brevity.

In any event, SFET and reference electrode die 410 includes a first SFET, a second SFET or REFET, and a reference electrode 442. The first SFET is formed in and over a substrate of a first conductivity type, and includes a first source 412, a first drain 414, a channel extending between the source and drain 412, 414, a gate dielectric 415 overlying the channel, and a sensing electrode 416 either overlying the gate dielectric 415 or electrically connected to a gate electrode that overlies the gate dielectric 415. Similarly, the REFET, which is formed in and over a well 424 with an opposite conductivity type from the substrate, includes a second source 418, a second drain 420, a channel extending between the source and drain 418, 420, a gate dielectric 421 overlying the channel, and a REFET electrode 422 either overlying the gate dielectric 421 or electrically connected to a gate electrode that overlies the gate dielectric 421. The electrodes 416, 422 are positioned proximate to an electrode-bearing surface of the SFET and reference electrode IC 410. In addition, in an embodiment, the SFET and reference electrode IC 410 includes sensitive material 417, 423 overlying either or both of the electrodes 416, 422.

According to the illustrated embodiment, the SFET and reference electrode IC 410 also includes a reference electrode 422 proximate to the electrode-bearing surface of the IC 410. The conductive components (e.g., electrodes 416, 422, 442) proximate to the electrode-bearing surface are electrically isolated from each other with passivation or protection layer 426, which also functions to protect the top surface of the substrate from the fluid 492 being tested.

The SFET and reference electrode IC 410 also includes a plurality of contacts 428 at or proximate to a contact surface of the SFET and reference electrode IC 410. The first SFET, the REFET, and the reference electrode 442 are electrically coupled to the contacts 428 through conductive traces of one or more metal layers and through TSVs, in various embodiments.

Package housing 460 includes a mounting surface 465 with contacts 466 that align with and are coupled to contacts 428 using solder balls 472 or other means. Contacts 466 are electrically coupled with additional contacts 468 at an exterior surface 469 of housing 460 through one or more routing layers and/or conductive vias.

As with the previously described embodiments, SFET device 400 also includes fluid barrier material 480 which is configured to provide a fluid barrier between contacts 428, 466 and a space that encompasses the sensing and REFET electrodes 416, 422 and the reference electrode 442, so that fluid 492 deposited within that space does not reach and short out the contacts 428, 466. As with the previously-described embodiments, the fluid barrier material 480 may be configured to maintain a cavity 476 between the SFET and reference electrode IC 410 and the mounting surface 465, or the fluid barrier material 480 may fill this cavity 476, as long as the fluid barrier material 480 is sufficiently electrically insulating.

In the embodiments illustrated and discussed in conjunction with FIGS. 2-4, the fluid barrier material 280, 380, 480 extends between sidewalls of the SFET and reference electrode ICs 210, 240, 310, 340, 410 and the mounting surface of the package housing 260, 360, 460. In an alternate embodiment, the fluid barrier material may take the form of seal ring(s) placed around the contact array(s) and between the contact surface(s) of the SFET and reference electrode IC(s) and the mounting surface of the package housing.

According to an embodiment, the shape and other characteristics of package housing 260, 360, 460 are configured to enable the sensing devices 200, 300, 400 to be coupled to or inserted into an external measurement system (e.g., measurement system 160, FIG. 1). For example, the measurement system may include contacts that align with package contacts (e.g., contacts 268, FIG. 2) when the SFET device 200, 300, 400 is suitably joined with the measurement system. The electrical connections between the SFET device 200, 300, 400 and the measurement system, once established, enable communication between those devices and provision of reference electrode biasing, as previously discussed.

In each of the above described embodiments, the SFET device 102, 200, 300, 400 has a FET/REFET configuration. In alternate embodiments, an SFET device may include only a single SFET. For example, each of the SFET ICs 210, 310, 410 may exclude the REFET altogether. In addition, in each of the above described embodiments, the SFET and the REFET have opposite conductivity types. In other alternate embodiments, the REFET may have the same conductivity type as the SFET, although with different physical and electrical characteristics and/or biases to facilitate differential sensing.

Figure 5:
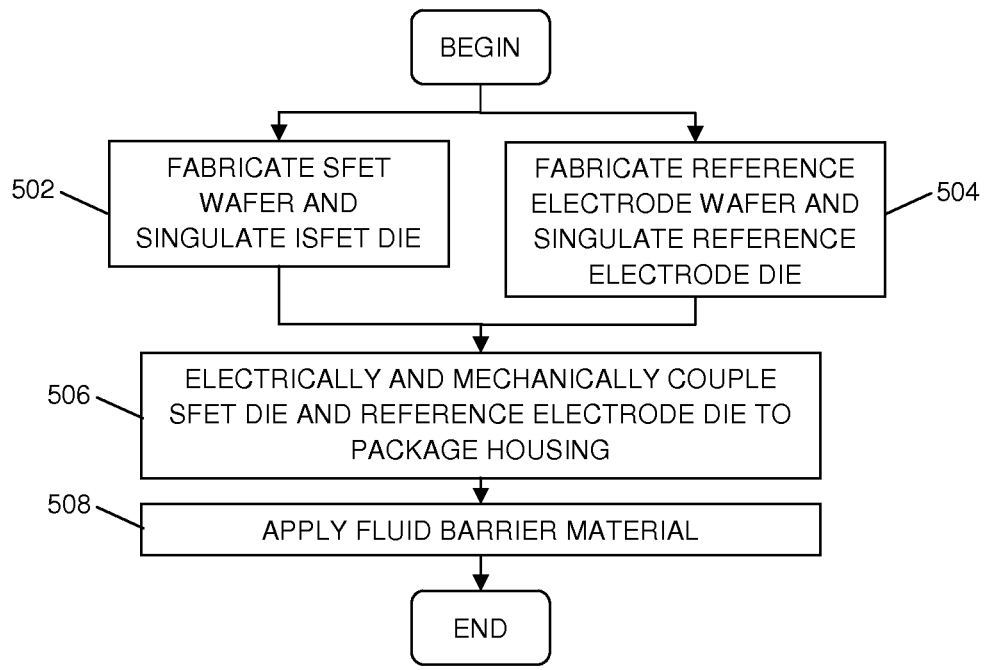
FIG. 5 is a flowchart of a method for fabricating an SFET device, in accordance with an example embodiment.

Embodiments of methods for fabricating and operating SFET devices will now be described in conjunction with FIGS. 5 and 6. Starting first with fabrication, FIG. 5 is a flowchart of a method for fabricating an SFET device (e.g., SFET devices 102, 200, 300, 400), in accordance with an example embodiment. The method may begin, in blocks 502 and 504, by fabricating an SFET wafer that includes a plurality of SFET IC die, and by separately fabricating a reference electrode wafer that includes a plurality of reference electrode IC die. By fabricating wafers that specifically include only reference electrode IC die or SFET IC die, processes that otherwise would be employed to ensure that sensitive materials are not deposited on the reference electrodes (or to ensure that deposited sensitive materials are removed from the reference electrodes) may be excluded from the fabrication process. In addition, the sensitive materials may be deposited across all SFET IC die prior to singulation of the SFET IC die from the wafer. Accordingly, in contrast to current practices in which sensitive materials are deposited on sensing and/or REFET electrodes individually after singulation, a relatively inexpensive and efficient spin coating or vapor/solution deposition process may be used at the wafer level to deposit the sensitive materials.

In any event, once the wafer-level fabrication of the SFET wafer and the reference electrode wafer are completed, a singulation process (e.g., wet sawing, laser cutting, or the like) may be performed to separate the individual SFET IC die and reference electrode IC die. In cases in which the sensitive materials may be compromised by conventional singulation techniques, singulation of the SFET IC die may be performed using a stealth dicing or other technique (e.g., focusing a laser beam into the interior of the semiconductor wafer, creating stresses that cause the die to separate when a mounting film is expanded). In an alternate embodiment, as discussed in conjunction with FIG. 4, the SFET(s) and reference electrodes may be included within a single die. In such cases, multiple SFET and reference electrode IC die may be included on a single wafer, and suitable masking and/or material removal processes may be employed to deposit the sensitive material on the SFET electrodes without leaving sensitive material on the reference electrodes.

In block 506, the SFET IC die and the reference electrode IC die (or the combined SFET and reference electrode IC die) are electrically and mechanically coupled to the mounting surface of a package housing, as described previously. In block 508, fluid barrier material is applied to provide a fluid barrier between contacts of the SFET and reference electrode IC die and the package housing, and a space that encompasses the sensing, REFET, and reference electrodes. As mentioned previously, one type of fluid barrier that may be employed is a seal ring. In such an embodiment, the seal ring may be fabricated on the SFET IC die and the reference electrode IC die at the wafer level (e.g., prior to singulation). Alternatively, the seal ring(s) may be applied during the process of coupling the SFET and reference electrode IC die to the mounting surface. Other fabrication processes also may be employed to complete the SFET device.

Figure 6:
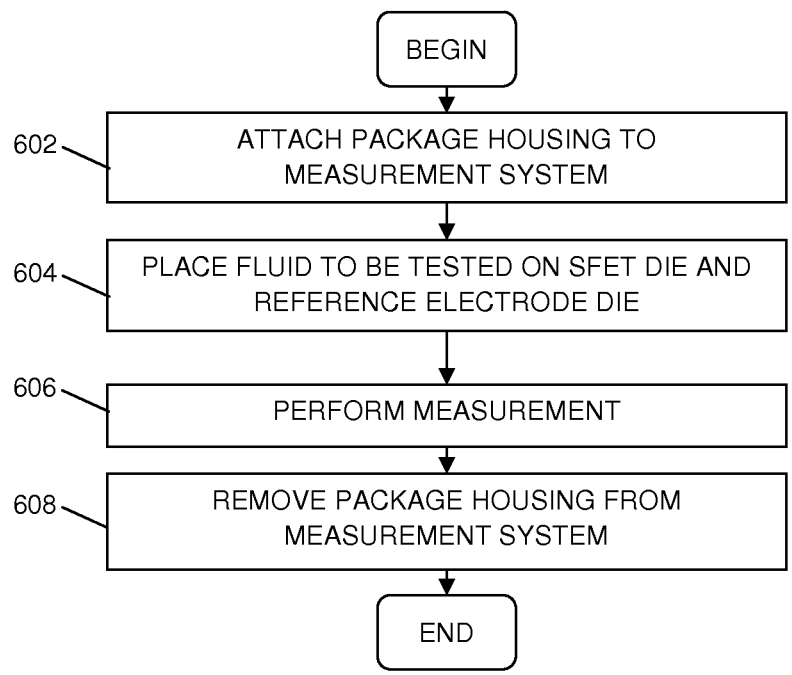
FIG. 6 is a flowchart of a method for using an SFET device to perform a measurement of a chemical substance or biological agent within a fluid.

FIG. 6 is a flowchart of a method for using an SFET device (e.g., any of devices 102, 200, 300, 400) to perform a measurement of a chemical substance or biological agent within a fluid. According to an embodiment, the SFET devices may be fabricated as distinct devices that may be removably or non-permanently coupled with an external measurement system (e.g., measurement system 160, FIG. 1). For example, as discussed previously, the shape and other characteristics of the package housing are configured to enable the SFET devices to be coupled to or inserted into the external measurement system. Accordingly, in an embodiment, the method for using an SFET device may begin, in block 602, by attaching the package housing of an SFET device to the measurement system. A calibration, self-test, or test using the measurement system optionally may be performed at this point.

In block 604, the fluid to be tested is placed on the SFET and reference electrode IC die, or more specifically in contact with the sensing electrode, the REFET electrode, and the reference electrode. Whether or not performed previously, a calibration, self-test, or test using the measurement system optionally may be performed at this point. In block 606, the measurement system may provide a bias voltage to the reference electrode, and the SFET IC die may produce a digital (or analog) value that indicates the presence of or concentration of ions or other substances within the fluid. In block 608, the SFET device may then be removed from the measurement system. For example, the SFET device may be a one-use only, disposable device. Alternatively, the SFET device may be suitable for multiple uses. In some cases, the SFET device may be sufficiently robust that it may be permanently coupled to the measurement system.

Various embodiments of SFET devices (or sensing devices), systems in which they are incorporated, and methods for their fabrication and use have been described above. For example, SFET devices may be used to sense the presence of or concentration of a target ion or molecule in a solution. When sensing biological material, a change in charge of a sensitive material overlying the sensing electrode occurs when the material to be measured bonds to the sensitive material. Examples include antigen-antibody bonding reactions, DNA bonding reactions, and a cell receptor bonding to its complement.

As described above, SFET transistors are used in the various embodiments of SFET devices, but the way they are used depends on the application. For ISFETS, the sensing electrode(s) (and thus the gate(s)) of the FET(s) interact with the electrolyte in which the SFET device is immersed, and a potential difference is developed between the gate(s) and the reference electrode. The resulting change in channel currents can be translated by an associated circuit to produce an analog or digital output that reflects the presence of or concentration of the relevant ions in the electrolyte. For example, the pH of a solution can be monitored by an SFET device with a sensitive material coating of silicon nitride. In addition, sodium (Na), potassium (K), magnesium (Mg), calcium (Ca), lead (Pb), and other chemicals or compounds may be detected by sensing electrodes made selective by polyvinyl chloride (PVC) based membranes.

In contrast, ENFETs have an enzyme coating. In many applications, the enzyme will interact with the analyte to create products which change the pH of the solution. This change in pH is detected by the SFET(s). A pair of SFETs may be used, one with the coating, and one without the coating as a reference. IMFETs use antibodies for coatings. A change in charge occurs when the antibodies interact with their targets. DNA sensors detect DNA strands in a similar fashion. A reference electrode may be excluded in either case.

An embodiment of a sensing device (or SFET device) includes first and second IC die, a housing, and a fluid barrier material. The first IC die includes a first electrode-bearing surface, a first contact surface on an opposite side of the first IC die from the first electrode-bearing surface, an SFET with a sensing electrode proximate to the first electrode-bearing surface, a plurality of first contacts at the first contact surface, and a plurality of first conductive structures coupled between the SFET and the first contacts. The second IC die includes a second electrode-bearing surface, a second contact surface on an opposite side of the second IC die from the second electrode-bearing surface, a reference electrode proximate to the second electrode-bearing surface, one or more second contacts at the second contact surface, and one or more second conductive structures coupled between the reference electrode and the one or more second contacts. The housing includes a mounting surface, and a plurality of third contacts formed at the mounting surface. The plurality of first contacts are coupled to a first set of the third contacts, and the one or more second contacts are coupled to a second set of the third contacts. The fluid barrier material is between the mounting surface and the first and second IC dies. The fluid barrier material provides a fluid barrier between the first, second, and third contacts and a space that encompasses the sensing electrode and the reference electrode.

Another embodiment of a sensing device (or SFET device) includes an IC die, a housing, and a fluid barrier material. The IC die includes an electrode-bearing surface, a contact surface on an opposite side of the IC die from the electrode-bearing surface, an SFET with a sensing electrode proximate to the electrode-bearing surface, a reference electrode proximate to the electrode-bearing surface, a plurality of first contacts at the contact surface, and a plurality of conductive structures coupled between the SFET, the reference electrode, and the first contacts. The housing includes a mounting surface, and a plurality of second contacts formed at the mounting surface. The plurality of first contacts are coupled to the second contacts. The fluid barrier material is between the mounting surface and the IC die. The fluid barrier material provides a fluid barrier between the first and second contacts and a space that encompasses the sensing electrode and the reference electrode.

An embodiment of a method of forming a sensing device (or SFET device) includes forming one or more IC die that include an SFET with a sensing electrode, a reference electrode, a plurality of first contacts at one or more contact surfaces, and a plurality of conductive structures coupled between the SFET, the reference electrode, and the first contacts. The method further includes coupling the plurality of first contacts to second contacts at a mounting surface of a housing, and providing a fluid barrier material between the mounting surface and the one or more IC die. The fluid barrier material provides a fluid barrier between the first and second contacts and a space that encompasses the sensing electrode and the reference electrode.

The connecting lines shown in the various figures contained herein are intended to represent exemplary functional relationships and/or physical couplings between the various elements. It should be noted that many alternative or additional functional relationships or physical connections may be present in an embodiment of the subject matter. In addition, certain terminology may also be used herein for the purpose of reference only, and thus are not intended to be limiting, and the terms "first", "second" and other such numerical terms referring to structures do not imply a sequence or order unless clearly indicated by the context.

The foregoing description refers to elements or nodes or features being "connected" or "coupled" together. As used herein, unless expressly stated otherwise, "connected" means that one element is directly joined to (or directly communicates with) another element, and not necessarily mechanically. Likewise, unless expressly stated otherwise, "coupled" means that one element is directly or indirectly joined to (or directly or indirectly communicates with, electrically or otherwise) another element, and not necessarily mechanically. Thus, although the schematic shown in the figures depict one exemplary arrangement of elements, additional intervening elements, devices, features, or components may be present in an embodiment of the depicted subject matter.

The various embodiments of the invention described here are illustrated by semiconductor devices and structures of particular conductivity type having various p and n doped regions appropriate for that conductivity type device or structure. But this is merely for convenience of explanation and not intended to be limiting. Persons of skill in the art will understand that devices or structures of opposite conductivity type may be provided by interchanging conductivity types so that a p-type region becomes an n-type region and vice versa. Alternatively, the particular regions illustrated in what follows may be more generally referred to as of a "first conductivity type" and a "second opposite conductivity type," wherein the first conductivity type may be either n or p type and the second opposite conductivity type is then either p or n type, and so forth. Further, for convenience of explanation and not intended to be limiting, various embodiments of the present invention are described herein for silicon semiconductors, but persons of skill in the art will understand the invention is not limited to silicon but applies to a wide variety of semiconductor materials. Non-limiting examples are other type IV semiconductor materials, as well as type III-V and II-VI semiconductor materials, organic semiconductor materials and combinations thereof, whether in bulk form or in layered form or in thin film form or semiconductor-on-insulator (SOI) form or combinations thereof. Such materials may be single-crystal or poly-crystalline or amorphous or combinations thereof.

The preceding detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, or detailed description.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A sensing device comprising:
   a first integrated circuit (IC) die that includes
      a first electrode-bearing surface,
      a first contact surface on an opposite side of the first IC die from the first electrode-bearing surface,
      a sensing field effect transistor (SFET) with a sensing electrode at the first electrode-bearing surface,
      a plurality of first contacts at the first contact surface, and
      a plurality of first conductive structures coupled between the SFET and the first contacts;
   a second IC die that is separate from the first IC die, wherein the second IC die includes
      a second electrode-bearing surface,
      a second contact surface,
      a reference electrode at the second electrode-bearing surface,
      one or more second contacts at the second contact surface, and
      one or more second conductive structures coupled between the reference electrode and the one or more second contacts;
   a housing that includes a mounting surface, sidewalls extending from the mounting surface, and a plurality of third contacts formed at the mounting surface, wherein the mounting surface and the sidewalls define a cavity that includes a space that encompasses the sensing and reference electrodes, and wherein the plurality of first contacts are coupled to a first set of the third contacts, and the one or more second contacts are coupled to a second set of the third contacts; and
   a fluid barrier material between the mounting surface and the first and second IC die, wherein the fluid barrier material provides a fluid barrier between the first, second, and third contacts and the space that encompasses the sensing and reference electrodes.

2. The sensing device of claim 1, wherein the fluid barrier material is selected from silicone, fluorosilicone, perfluoropolyether, epoxy, polyurethane, an underfill material, a gel, and seal rings between the first and second contact surfaces and the mounting surface.

3. The sensing device of claim 1, wherein the first IC die further includes:
   a substrate having an active surface and a first conductivity type, and
   wherein the SFET includes a first source formed at the active surface and having a second conductivity type, a first drain formed at the active surface and having the second conductivity type, a first channel at the active surface between the first source and the first drain, and a first dielectric overlying the first channel.

4. The sensing device of claim 3, further comprising a reference FET (REFET) that includes a well formed in the substrate that extends to the active surface and has the second conductivity type, a second source formed in the well and having the first conductivity type, a second drain formed in the well and having the first conductivity type, a second channel between the second source and the second drain, and a second dielectric overlying the second channel.

5. The sensing device of claim 4, wherein the first IC die further includes:
   a first measurement device having first inputs coupled to the first source and the first drain, and a first output that produces a first signal representing a voltage or current between the first source and the first drain;
   a second measurement device having second inputs coupled to the second source and the second drain, and a second output that produces a second signal representing a voltage or current between the second source and the second drain; and
   an operational amplifier having third inputs coupled to the first and second outputs, and a third output that produces a third signal representing a difference between the first signal and the second signal.

6. The sensing device of claim 5, wherein the first IC die further includes:

a microcontroller coupled to the third output and configured to convert the third signal into a digital signal.

7. The sensing device of claim 6, wherein the first IC die further includes:
a digital interface coupled between the microcontroller and the plurality of first contacts, and configured to output the digital signal produced by the microcontroller.

8. The sensing device of claim 1, wherein the SFET further includes a sensitive material deposited on the sensing electrode, wherein the sensitive material is selected from a biological material sensitive material, a pH sensitive material, a chemical sensitive material, and an ion sensitive material.

9. The sensing device of claim 8, wherein the sensitive material includes one or more materials that are selected from silicon nitride, polyvinyl chloride (PVC) based membranes, an enzyme, an antibody, an antigen, ribonucleic acid (RNA), deoxyribonucleic acid (DNA), DNA-like fragments, epitopes, and cell receptors.

10. The sensing device of claim 1, wherein the plurality of first and second conductive structures comprise through substrate vias.

11. A sensing device comprising:
an integrated circuit (IC) die that includes
an electrode-bearing surface,
a contact surface on an opposite side of the IC die from the electrode-bearing surface,
a sensing field effect transistor (SFET) with a sensing electrode at the electrode-bearing surface,
a reference electrode,
a plurality of first contacts at the contact surface, and
a plurality of conductive structures coupled between the SFET, the reference electrode, and the first contacts;

a housing that includes a mounting surface, sidewalls extending from the mounting surface, an exterior surface opposite the mounting surface, a plurality of second contacts formed at the mounting surface, and a plurality of third contacts formed at the exterior surface, wherein the plurality of first contacts are coupled to the second contacts, and the plurality of second contacts are electrically coupled through the housing to the plurality of third contacts through one or more conductive routing layers and conductive vias, and wherein the mounting surface and the sidewalls define a cavity that includes a space that encompasses the sensing and reference electrodes; and a fluid barrier material between the mounting surface and the IC die, wherein the fluid barrier material provides a fluid barrier between the first and second contacts and the space that encompasses the sensing and reference electrodes.

12. The sensing device of claim 11, wherein the fluid barrier material is selected from silicone, fluorosilicone, perfluorpolyether, epoxy, polyurethane, an underfill material, a gel, and a seal ring between the contact surface and the mounting surface.

13. The sensing device of claim 11, wherein the IC die further comprises a reference FET (REFET).

14. The sensing device of claim 11, wherein the SFET further includes a sensitive material deposited on the sensing electrode, wherein the sensitive material is selected from a biological material sensitive material, a pH sensitive material, a chemical sensitive material, and an ion sensitive material.

* * * * *